United States Patent [19]

Broecker et al.

[11] 4,393,251
[45] Jul. 12, 1983

[54] PREPARATION OF PROPANEDIOLS USING A COPPER-AND ZINC CONTAINING HYDROGENATION CATALYST

[75] Inventors: Franz J. Broecker, Ludwigshafen; Leopold Hupfer, Friedelsheim; Franz Merger, Frankenthal; Ernest Miesen, Ludwigshafen; Juergen Paetsch, Wachenheim; Guenter Zirker, Ludwigshafen, all of Fed. Rep. of Germany

[73] Assignee: BASF Aktiengesellschaft, Ludwigshafen, Fed. Rep. of Germany

[21] Appl. No.: 347,380

[22] Filed: Feb. 10, 1982

Related U.S. Application Data

[62] Division of Ser. No. 274,486, Jun. 17, 1981.

[51] Int. Cl.$^3$ .................... C07C 31/20; C07C 33/26; C07C 31/27; C07C 41/26
[52] U.S. Cl. .................................. 568/811; 568/644; 568/650; 568/831; 568/838; 568/862
[58] Field of Search ............... 568/862, 831, 811, 838, 568/644, 650

[56] References Cited

U.S. PATENT DOCUMENTS

| | | | |
|---|---|---|---|
| 2,549,416 | 4/1951 | Brooks | 568/881 |
| 3,808,280 | 4/1974 | Merger et al. | 568/862 |
| 4,052,467 | 10/1977 | Mills et al. | 568/882 |
| 4,298,766 | 11/1981 | Broecker et al. | 568/862 |

FOREIGN PATENT DOCUMENTS

| | | | |
|---|---|---|---|
| 8767 | 3/1980 | European Pat. Off. | 568/881 |
| 988316 | 4/1965 | United Kingdom | 568/831 |

*Primary Examiner*—Joseph E. Evans

*Attorney, Agent, or Firm*—John H. Shurtleff

[57] ABSTRACT

Hydrogenation catalysts which are prepared from mixed crystals of copper-zinc compounds, obtained by precipitation, of the formula

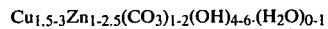

by decomposition at 200°–500° C., and are used for the catalytic preparation of propanediols of the formula

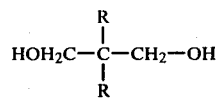

where the R's may be identical or different and each is an aliphatic, araliphatic or aromatic radical, or the two R's together with the adjacent carbon atom are members of an alicyclic ring, by hydrogenating hydroxypropionaldehydes of the formula

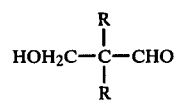

where R has the above meanings, and to processes for the preparation of propanediols, using such catalysts. The propane-1,3-diols obtainable by the novel process are valuable starting materials for the preparation of lubricants, plastics, surface coatings and synthetic resins, for example of polyesters derived from the propanediols.

9 Claims, No Drawings

PREPARATION OF PROPANEDIOLS USING A COPPER-AND ZINC CONTAINING HYDROGENATION CATALYST

This is a division of application Ser. No. 274,486, filed June 17, 1981.

The present invention relates to hydrogenation catalysts which are prepared from mixed crystals of copper-zinc compounds, obtained by precipitation, of the formula $Cu_{1.5-3}Zn_{1-2.5}(CO_3)_{1-2}(OH)_{4-6}\cdot(H_2O)_{0-1}$ by decomposition at 200°–500° C., and are used for the catalytic preparation of propanediols of the formula

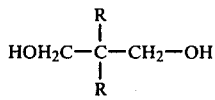   I where the R's may be identical or different and each is an aliphatic, araliphatic or aromatic radical, or the two R's together with the adjacent carbon atom are members of an alicyclic ring, by hydrogenating hydroxypropionaldehydes of the formula

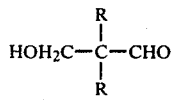   II where R has the above meanings, and to processes for the preparation of propanediols, using such catalysts.

The hydrogenation of hydroxypivalaldehyde is conventionally carried out in a liquid phase at pressures of from 100 to 200 bar and at up to 150° C., using a nickel, nickel-copper or cobalt catalyst (German Published Application DAS No. 1,014,089).

German Laid-Open Application DOS No. 1,804,984 describes the hydrogenation at 175°–220° C. and 64–704 bar in the presence of a copper chromite catalyst. This publication points out (page 10, last paragraph) that the choice of the catalyst employed is critical, since the hydrogenation is carried out in the presence of formaldehyde and water, and most conventional hydrogenation catalysts are deactivated by formaldehyde. Furthermore, the activity of the catalyst and the stability of most carriers is adversely affected by water. Using nickel and cobalt catalysts, undesired by-products are formed under the stated conditions, and this has an adverse effect on the yield and purity of the neopentyl glycol.

In another process (British Pat. No. 1,048,530), 2,2-dimethyl-3-hydroxypropanal is hydrogenated simultaneously with isobutyraldehyde in the presence of a copper/chromium oxide catalyst. Here again, numerous by-products are formed to a substantial degree. The need to process further the isobutanol formed adversely affects the economics.

To achieve satisfactory yields, it is necessary to employ severe hydrogenation conditions and expensive recycling. The working up of the aqueous phase, or its disposal, which entails substantial loss of material, is equally expensive.

German Published Application DAS No. 1,957,551 discloses that neopentyl glycol can be prepared by reacting isobutyraldehyde and formaldehyde in the presence of a basic catalyst and then hydrogenating the resulting 2,2-dimethyl-3-hydroxypropanal in the presence of a hydrogenation catalyst. The catalysts mentioned are cobalt, copper, manganese and/or nickel catalysts, for example sintered catalysts. Preferably, phosphoric acid is also present. In the Examples given, high hydrogenation temperatures are employed, as only these give satisfactory space-time yields.

We have found novel hydrogenation catalysts for the preparation of propanediols of the formula

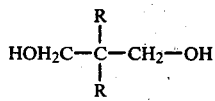   I where the R's may be identical or different and each is an aliphatic, araliphatic or aromatic radical, or the two R's together with the adjacent carbon atom are members of an alicyclic ring, by hydrogenating hydroxypropionaldehydes of the formula

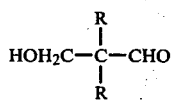   II where R has the above meanings, in the presence of a copper-containing hydrogenation catalyst, which novel catalysts are obtained by precipitating copper and zinc in a ratio of from 0.6 to 3 atoms of copper per atom of zinc from their compounds in the presence of a carbonate at a pH of from 6.9 to 8, and decomposing the resulting mixed crystals of the formula

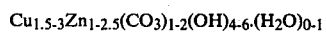

at from 200° to 500° C.

Further, we have found that propanediols of the formula

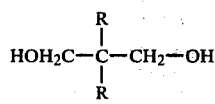   I where the R's may be identical or different and each is an aliphatic, araliphatic or aromatic radical, or the two R's together with the adjacent carbon atom are members of an alicyclic ring, are obtained in an advantageous manner by hydrogenating hydroxypropionaldehydes of the formula

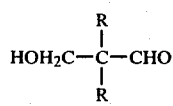   II where R has the above meanings, if the hydrogenation is carried out with a copper-containing hydrogenation catalyst which has been obtained by precipitating copper and zinc in a ratio of from 0.6 to 3 atoms of copper per atom of zinc from their compounds in the presence of a carbonate at a pH of from 6.9 to 8, and decomposing the resulting mixed crystals of the formula

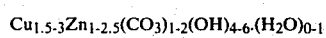

at from 200° to 500° C.

Where hydroxypivalaldehyde is used, the reaction can be represented by the equation:

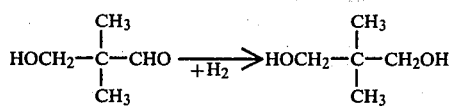

$$\underset{\underset{CH_3}{|}}{\overset{\overset{CH_3}{|}}{HOCH_2-C-CHO}} \xrightarrow{+H_2} \underset{\underset{CH_3}{|}}{\overset{\overset{CH_3}{|}}{HOCH_2-C-CH_2OH}}$$

Compared to the conventional processes, the process according to the invention gives propanediols, especially neopentyl glycol, more simply and more economically, in good yield and high purity, without significant formation of by-products, for example esters and acetals, and decomposition products. Additional purification operations, or additives which must be removed before hydrogenation, are not needed. The high hydrogenation activity of the novel catalyst makes it possible to carry out the hydrogenation at a low temperature, so that, for example, hydrogenolytic cleavage of the neopentyl glycol formed does not occur. The reverse decomposition of hydroxypivalaldehyde to isobutyraldehyde and formaldehyde also does not occur. All these advantageous results, and especially the low degree of ester formation, are surprising, since zinc oxide is known to be a good catalyst for forming neopentyl glycol hydroxypivalate (German Pat. No. 2,234,110). Compared to German Published Application DAS No. 1,957,591, the novel process offers the advantage that the crude untreated hydroxypivalaldehyde can be hydrogenated, at a low temperature and low pressure, in the liquid phase, with a high space-time yield. The catalyst has a high activity and long life, and is mechanically stable.

An essential feature of the process according to the invention is that the hydrogenation catalyst is prepared from mixed crystals having a specific structure; this structure ensures that in the subsequent thermal decomposition (calcination), the fine state of division is maintained and a specific configuration of copper and zinc in the finished, ie. calcined, catalyst is obtained. It is this configuration which is responsible for the advantageous results according to the invention. The copper/zinc/$CO_3$/OH mixed crystals obtained by precipitation have a defined and measurable crystal lattice. Preferably, the crystals are present in a monoclinic crystal system. The individual lattice positions are occupied by copper and zinc and by the $CO_3$ and OH radicals, and additives, as a rule in an amount of from 0 to 10, especially from 0 to 5, percent by weight, based on the total catalyst, can also occupy lattice positions. Advantageous additives to use are chromium, calcium, magnesium and, preferably, aluminum, which are incorporated, in the form of carbonates, hydroxides or oxides, as lattice points, or occupy defect positions; where appropriate, the additives can also be calcined, in an amorphous or crystalline form, as a component of a mixture with the mixed crystals according to the invention. In the mixed crystals, the components according to the invention are present in a ratio of 1.5–3, especially 1.75–2.5, atoms of copper: 1–2.5, especially 1.5–2.25, atoms of zinc: 1–2 equivalents of $CO_3$: 4–6 equivalents of OH. Mixed crystals which in their lattice structure correspond to hydrozincite and especially to malachite and zinc hydroxycarbonate are preferred.

The invention is based on the observation that on precipitation of copper and zinc hydroxycarbonates, mixed crystals are formed, depending on the pH conditions and the atomic ratio of copper and zinc. If copper predominates in the solution to be precipitated, a mixed crystal which has one of the above crystal lattices, for example that of malachite, is formed, whilst if the zinc content predominates, a mixed crystal which has one of the above crystal lattices, for example the crystal lattice of zinc hydroxycarbonate, is formed. Accordingly, in malachite, $CuCO_3.Cu(OH)_2$, some of the copper ions can be replaced by zinc ions, whilst in a zinc hydroxycarbonate, for example $ZnCO_3.3Zn(OH)_2.H_2O$, some of the zinc ions can be replaced by copper ions. The preparation of these mixed crystal compounds ensures optimum distribution of the active components. On decomposition of the hydroxycarbonates during calcination, this distribution is retained in the oxide mixture.

Preferred starting materials II and, accordingly, preferred end products I are those where the R's are identical or different and each is alkyl of 1 to 6 carbon atoms, aralkyl or alkylaryl, each of 7 to 12 carbon atoms, or phenyl, or the two R's together with the adjacent carbon atom are members of a 5-membered or 6-membered alicyclic ring. The above radicals and rings can additionally be substituted by groups which are inert under the reaction conditions, for example alkyl or alkoxy, each of 1 to 4 carbon atoms.

Examples of suitable starting materials II are 3-hydroxyprionaldehyde which has two identical or different substituents, chosen from methyl, ethyl, propyl, isopropyl, butyl, isobutyl, sec.-butyl, tert.-butyl, benzyl, phenyl, 2-methylphenyl, 3-methylphenyl, 4-methylphenyl, 3-methoxyphenyl, 2-methoxyphenyl and 4-methoxyphenyl, in the 2-position, as well as 1-formyl-1-methylolcyclohexane and 1-formyl-1-methylolcyclopentane.

Precipitation is advantageously effected by mixing the solutions of the copper and zinc compounds and of the additives, preferably of aluminum compounds. It is true that the additives can also be subsequently introduced into the precipitation mixture, or be mixed with the mixed crystals before calcination, or with the catalyst particles after calcination. As a rule, however, they are added in the form of solutions, and precipitated together with the copper and zinc. To ensure minimum recrystallization during calcination, it is advantageous to precipitate the additives in the form of structural promoters or stabilizers, for example aluminum oxide or chromium oxide, together with the mixed crystals. Advantageously, the precipitation is effected from aqueous solutions, and using correspondingly water-soluble compounds of the metals. Examples of suitable compounds are the acetates, formates, chlorides, bromides, iodides, sulfates, hydroxides, carbonates, bicarbonates, bisulfates, phosphates, hydrogen phosphates, dihydrogen phosphates, nitrites and, in particular, nitrates of copper, zinc and the additive metals. The carbonate radicals required in the mixed crystals can be introduced into the precipitation mixture as carbonates of copper, zinc or of the additive metals or, advantageously, in the form of added alkali metal carbonates or alkali metal bicarbonates, for example the potassium or sodium salts, which serve to set up the pH required according to the invention. Advantageously, the mixed crystals used according to the invention are prepared from two aqueous solutions, of which solution 1 contains the nitrates of copper, zinc and the additive metals, for example aluminum, in the atomic ratio specified above, whilst solution 2 is an aqueous sodium carbonate solution. Advantageously, 1–2 molar solutions of the metal compounds and 1–2 molar carbonate solutions or bicarbonate solutions are employed. The precipitation is advantageously carried out at from 5° to 90° C., preferably from 20° to 90° C., advantageously from 40° to 85° C., especially from 60° to 80° C., for 1–2 hours, batchwise or continuously, under atmospheric or superatmospheric pressure, at a pH of from 7 to 8, especially from 7 to 7.5. Preferably, both solutions are heated to the precipitation temperature and then fed into a stirred kettle. In this parallel precipitation method, the pH specified above is maintained by regulating the feed rates. The pH according to the invention must be maintained from the start and throughout the precipitation period. The precipitate formed is then advantageously stirred for a further 15–60 minutes at a pH of from 7 to 7.5, especially at pH 7, after which it is filtered off and washed salt-free, for example nitrate-free, with water. The mixed crystals formed by precipitation can rapidly be tested by taking Debye-Scherrer X-ray diagrams. The washed precipitate is then dried, advantageously at 100°–200° C., after which it is calcined, advantageously at 250°–500° C. and preferably at 300°–400° C., advantageously for from 2 to 5 hours. It is then advantageous to convert the oxide catalyst to the desired shape, for example by molding it into pills or extrudates. After molding, the catalyst is advantageously heated again at 200°–500° C., especially 300°–500° C. The resulting catalyst is then introduced into the hydrogenation reactor. In a preferred embodiment, it is subsequently activated at 150°–250° C., using a mixture of 0.5–30 parts by volume of hydrogen and 99.5–70 parts by volume of nitrogen. After the activation, the catalyst is advantageously wetted with water or with the hydrogenation mixture, containing propanediol.

The hydrogenation of the hydroxypropionaldehyde II is carried out batchwise or continuously, advantageously at from 80° to 260° C., preferably from 100° to 175° C., especially from 110° to 150° C., under a pressure of from 1 to 300 bar, preferably from 10 to 200 bar, especially from 20 to 100 bar.

In batchwise hydrogenation, the catalyst is as a rule employed in an amount of from 1 to 10, especially from 2 to 5, percent by weight, based on hydroxypropionaldehyde, with a reaction time of from 0.1 to 5 hours.

The continuous hydrogenation is advantageously carried out by conventional methods, for example by a bottom-phase reaction or trickle method, in a fixed bed reactor, at the stated temperatures and pressures. Hydroxypropionaldehyde II is introduced, under the preferred conditions, advantageously by means of injection pumps, continuously into the reactor in an amount of from 0.1 to 5 parts per liter of catalyst per hour. The material leaving the reactor is either introduced directly into a continuous fractionation column or is collected in stock vessels and fractionated batchwise. In general, the distillation pressure is chosen to be such that the boiling point of the end product is above its melting point (129° C.), ie. the pressure is above 50 mbar.

In a preferred embodiment, instead of using the starting material II, the reaction mixture from its preparation is employed; for example, isobutyraldehyde and formaldehyde are reacted, advantageously in an amount of from 0.1 to 1.5, more especially from 0.9 to 1.1, moles of formaldehyde per mole of isobutyraldehyde, in the presence of a tertiary amine catalyst, advantageously at from 20° to 100° C., under atmospheric or superatmospheric pressure, batchwise, for example for from 0.1 to 4 hours, or continuously, and the resulting reaction mixture is employed in place of hydroxypivalaldehyde in the process according to the invention.

The propane-1,3-diols obtainable by the novel process are valuable starting materials for the preparation of lubricants, plastics, surface coatings and synthetic resins, for example polyesters corresponding to the propanediols. Regarding the use of the products, reference may be made to the publications monitored and to Ullmanns Encyklopädie der technischen Chemie, Volume 15, pages 292 et seq.

In the Examples, parts are by weight and bear the same relation to parts by volume as that of the kilogram to the liter.

EXAMPLE 1

(a) Preparation of the catalyst: The catalyst is prepared from an aluminum-containing mixed crystal material of the zinc hydroxide-carbonate type (4 ZnO.CO$_2$.4H$_2$O). The compound, modified with aluminum oxide, and having the following composition of the mixed crystals $$Cu_{1.76}Zn_{2.24}(CO_3)(OH)_6.H_2O$$

is prepared from two solutions:

Solution 1: 7.200 parts of Cu(NO$_3$)$_2$.3H$_2$O, 11.370 parts of Zn(NO$_3$)$_2$.6H$_2$O and 1.473 parts of Al(NO$_3$)$_2$.9H$_2$O are dissolved in water. The solution is made up to 36 parts by volume with water.

Solution 2: 37 parts by volume of an aqueous solution containing 7.850 parts of sodium carbonate are prepared.

The two solutions are separately heated to 80° C. Precipitation is then carried out in a stirred kettle into which 10 parts by volume of water at 80° C. are initially introduced. The mixed crystals are precipitated by running solutions 1 and 2 in parallel into the kettle, with vigorous stirring. A pH of 7 is maintained in the stirred kettle over the entire precipitation period (about 1 hour) by accurately regulating the feed speeds. The pH is monitored with a glass electrode.

After completion of the precipitation, the mixture is stirred for a further 30 minutes at 80° C. and the precipitate is then filtered off and washed nitrate-free. A sample of the mixed crystal precipitate is examined by taking a Guinier X-ray diagram. The mixed crystal compound has the following characteristic d-values of the diffraction lines: 6.76; 3.71; 3.20; 2.89; 2.75; 2.63; 2.16; 1.95; 1.60.

The filter cake is dried at 110° C. and is then calcined for 5 hours at 300° C. The resulting oxide product is comminuted to a particle size of less than 1 mm 2 percent by weight of graphite are added and the mixture is molded to form pills.

(b) Hydrogenation: 2 parts of the catalyst prepared as described in (a), in the form of 5 mm×5 mm pills, are introduced into a hydrogenation reactor and reduced at atmospheric pressure and 180° C. by means of 500 parts by volume of a mixture of 5 percent by volume of H$_2$ and 95 percent by volume of N$_2$. After it has been activated, the catalyst is cooled to 100° C., and one part per hour of a 60 percent strength by weight aqueous solution of hydroxypivalaldehyde (the latter being 98% pure and containing isobutyraldehyde and formaldehyde as impurities) is passed, from a vessel, through the reactor, heated and hydrogenated at 130° C. for 30 bar. The throughput is 0.3 part of hydroxypivalaldehyde per liter of catalyst per hour. The conversion is 99 percent. The hydrogenated material is separated from the catalyst by filtration, and is fractionated in a column with glass packings. At 90 mbar, after first runnings of water and small amounts of methanol, isobutanol and hydroxypivalaldehyde, neopentyl glycol, of boiling point 138°–140° C. (melting point 128°–129° C., the ester content of the material being less than 0.1 percent by weight) is obtained in an amount corresponding to 0.5965 part per hour of reaction time. This corresponds to a yield of 97.5% of theory, based on starting material.

EXAMPLE 2

(a) Preparation of the catalyst: To prepare a copper-rich catalyst, an aluminum-containing mixed crystal material of the malachite type, having the following empirical formula, is prepared:

$$Cu_{1.2}Zn_{0.8}(CO_3)(OH)_2$$

As in Example 1(a), two solutions are used for the precipitation.

Solution 1: 14.790 parts of $Cu(NO_3)_2.3H_2O$, 11.540 parts of $Zn(NO_3)_2.6H_2O$ and 2.240 parts of $Al(NO_3)_3.9H_2O$ are dissolved in water. The solution is made up to 32 parts by volume with water.

Solution 2: 8.060 parts of sodium carbonate are dissolved in 32 parts by volume of water.

The two solutions are heated to 80° C. and combined, at pH 7, by regulated parallel introduction, in the course of 45 minutes, into a stirred kettle which initially contains 8 parts by volume of water at 80° C. The precipitate obtained is filtered off, washed nitrate-free and dried at 110° C.

According to a Debye-Scherrer diagram, the dried product is a single compound having the following d-values of the X-ray diffraction lines, listed in the sequence of their intensities: 3.70; 2.72; 5.10; 6.10; 2.45; 2.55; 7.60; 3.00; 6.90; 2.68; 2.32; 2.18; 1.64; 1.52.

After having been dried, the mixed crystals are calcined for 7 hours at 300° C. and then mixed with 2 percent by weight of graphite, after which the mixture is molded into pills. The pills are then calcined for a further 3 hours at 300° C.

(b) Hydrogenation: A hydrogenation is carried out, and the reaction mixture worked up, by a method similar to that of Example 1(b).

2(b)(1) The hydrogenation is carried out at 110° C. with a throughput of 0.3 part of hydroxypivalaldehyde per liter of catalyst per hour (98% conversion). Fractional distillation gives neopentyl glycol, of melting point 129° C., in an amount corresponding to 0.5934 part per hour. This corresponds to a yield of 97% of theory, based on starting material.

2(b)(2) The hydrogenation is carried out at 130° C. 99% conversion is achieved, and fractional distillation gives neopentyl glycol, of melting point 129° C., in an amount corresponding to 0.5995 part per hour. This corresponds to a yield of 98% of theory, based on starting material.

2(b)(3) 0.6 part of hydroxypivalaldehyde per liter of catalyst per hour is hydrogenated under the conditions of Example 2(b)(2). 87% conversion is achieved, and fractional distillation, after removing first runnings and starting material which can be recycled, gives neopentyl glycol, of melting point 128°–129° C., in an amount corresponding to 1.0474 part per hour. This corresponds to a selectivity of 98.4%, based on converted starting material.

EXAMPLE 3

The catalyst described in Example 1(a) is employed in a circulatory hydrogenation reactor for 1,000 hours at 110° C. under a pressure of 30 bar with a throughput of 0.3 part of hydroxypivalaldehyde per liter of catalyst per hour.

The hydrogenation and working up are carried out similarly to Example 1(b). The conversion is 98% and remains constant over 1,000 operating hours, there also being no loss of activity of the catalyst.

Fractional distillation gives neopentyl glycol, of melting point 128°–129° C., in an amount which over the entire operating time corresponds to 0.5933 part per liter of catalyst per hour. This is equivalent to a yield of 97%, based on starting material.

EXAMPLE 4

Using the method described in Example 1(b), one part per hour of a 70 percent strength by weight aqueous solution of 2-methyl-2-ethyl-3-hydroxypropanal is hydrogenated, over the catalyst prepared as described in Example 1(a), at 130° C. and 30 bar, with a throughput of 0.35 part of 2-methyl-2-ethyl-3-hydroxypropanal per liter of catalyst per hour. The conversion is 99 percent. The hydrogenated material is fractionated through a packed column. After first runnings of water and small amounts of methanol, 2-methylbutanol and 2-methyl-2-ethyl-3-hydroxypropanal, 2-methyl-2-ethyl-propane-1,3-diol, of boiling point of 110°–112° C./12 mbar (melting point 44°–46° C.), is obtained in an amount corresponding to 0.6850 part per hour. This is equivalent to a yield of 96.2% of theory, based on starting material.

EXAMPLE 5

Using the method described in Example 1(b), 1.4 parts per hour of a 60 percent strength by weight solution of 1-hydroxymethyl-hexahydro-benzaldehyde in a 1:1 water-methanol mixture are hydrogenated, over the catalyst prepared as described in Example 1(a), at 130° C. and 30 bar, with a throughput of 0.42 part of 1-hydroxymethyl-hexahydrobenzaldehyde per liter of catalyst per hour. The conversion is 99 percent. The hydrogenated material is fractionated through a packed column. After first runnings of water, methanol and small amounts of hexahydrobenzyl alcohol and 1-hydroxymethyl-hexahydrobenzaldehyde, 1,1-dihydroxymethylcyclohexane, of boiling point 120°–122° C./3 mbar (melting point 90°–92° C.), is obtained in an amount corresponding to 0.8314 part per hour. This is equivalent to a yield of 97.6% of theory, based on starting material.

EXAMPLE 6

Using the method described in Example 1(b), one part per hour of a 72 percent strength by weight aqueous solution of 2-methyl-2-propyl-3-hydroxypropanal is hydrogenated, over the catalyst prepared as described in Example 1(a), at 130° C. and 30 bar, with a throughput of 0.36 part of 2-methyl-2-propyl-3-hydroxypropanal per liter of catalyst per hour. The conversion is 89.5 percent. The hydrogenated material is fractionated through a packed column. After first runnings of water and small amounts of methanol, 2-methylpentanal and 2-methyl-2-propyl-3-hydroxypropanal, 2-methyl-2-propyl-propane-1,3-diol, of boiling point 112°–113° C./5 mbar (melting point 58°–60° C.), is obtained in an amount corresponding to 0.6967 part per hour. This is equivalent to a yield of 95.3% of theory, based on starting material.

EXAMPLE 7

Using the method described in Example 1(b), 1.2 parts per hour of a 50 percent strength by weight solution of 2-methyl-2-phenyl-3-hydroxypropanal in a 1:1 water-methanol mixture are hydrogenated, over the catalyst prepared as described in Example 1(a), at 130° C. and 30 bar, with a throughput of 0.3 part of 2-methyl-2-phenyl-3-hydroxypropanol per liter of catalyst per hour. The conversion is over 99 percent. The hydrogenated material is fractionated through a packed column. After first runnings of water, methanol, 2-phenyl-propanol and 2-methyl-2-phenyl-3-hydroxypropanal, 2-methyl-2-phenyl-propane-1,3-diol, of boiling point 143°–145° C./1 mbar (melting point 80°–82° C.), is obtained in an amount corresponding to 0.5405 part per hour. This is equivalent to a yield of 89% of theory, based on starting material.

We claim:

1. In a process for the preparation of a propanediol of the formula

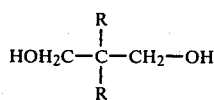

where the R's may be identical or different and each is an aliphatic, araliphatic or aromatic radical, or the two R's together with the adjacent carbon atom are members of an alicyclic ring, by hydrogenating a hydroxypropionaldehyde of the formula

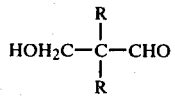

where R has the above meanings, in the presence of a copper-containing hydrogenation catalyst, the improvement which comprises:

carrying out the hydrogenation in the liquid phase with a hydrogenation catalyst which has been obtained by precipitating copper and zinc in a ratio of from 0.6 to 3 atoms of copper per atom of zinc from a solution of their compounds in the presence of a carbonate at a pH of from 6.9 to 8, and decomposing the resulting mixed crystals of the formula $$Cu_{1.5-3}Zn_{1-2.5}(CO_3)_{1-2}(OH)_{4-6}\cdot(H_2O)_{0-1}$$

at from 200° to 500° C., introducing into said catalyst during its preparation at least one metal additive selected from the group consisting of chromium, calcium, magnesium and aluminum in an amount of up to 10 percent by weight, based on the total catalyst.

2. A process as claimed in claim 1, wherein the reaction is carried out with 1–2 molar solutions of the metal compounds and 1–2 molar carbonate or bicarbonate solutions.

3. A process as claimed in claim 1, wherein the precipitation is carried out at from 5° to 90° C.

4. A process as claimed in claim 1, wherein the precipitation is carried out at a pH of from 7 to 8.

5. A process as claimed in claim 1, wherein the decomposition of the mixed crystals is carried out at from 300° to 400° C.

6. A process as claimed in claim 1, wherein the catalyst is activated at from 150° to 250° C. with a mixture of from 0.5 to 30 parts by volume of hydrogen and from 99.5 to 70 parts by volume of nitrogen.

7. A process as claimed in claim 1, wherein the hydrogenation is carried out at from 80° to 260° C.

8. A process as claimed in claim 1, wherein the hydrogenation is carried out at a pressure of from 1 to 300 bar.

9. A process as claimed in claim 1, wherein the hydrogenation is carried out with from 1 to 10 percent by weight of hydrogenation catalyst, based on hydroxypropionaldehyde II.

* * * * *